(12) United States Patent
Ge et al.

(10) Patent No.: US 9,681,926 B2
(45) Date of Patent: Jun. 20, 2017

(54) MEDICAL PENDANT LIFTING SYSTEM

(71) Applicant: MAQUET (SUZHOU) CO. LTD., Suzhou (CN)

(72) Inventors: Kaiyou Ge, Suzhou (CN); Bing Wei, Suzhou (CN); Qunhua Li, Suzhou (CN); Hongqiang Li, Suzhou (CN); Ming Ji, Suzhou (CN)

(73) Assignee: MAQUET (SUZHOU) CO.LTD., Suzhou (CN)

( * ) Notice: Subject to any disclaimer, the term of this patent is extended or adjusted under 35 U.S.C. 154(b) by 25 days.

(21) Appl. No.: 14/907,465

(22) PCT Filed: Jul. 25, 2014

(86) PCT No.: PCT/CN2014/082975
§ 371 (c)(1),
(2) Date: Jan. 25, 2016

(87) PCT Pub. No.: WO2015/014240
PCT Pub. Date: Feb. 5, 2015

(65) Prior Publication Data
US 2016/0184048 A1 Jun. 30, 2016

(30) Foreign Application Priority Data

Aug. 2, 2013 (CN) .......................... 2013 1 0333198
Jul. 16, 2014 (CN) .......................... 2014 1 0339398

(51) Int. Cl.
*E04G 3/00* (2006.01)
*A61B 90/50* (2016.01)
*F16M 13/02* (2006.01)

(52) U.S. Cl.
CPC ........... *A61B 90/50* (2016.02); *F16M 13/027* (2013.01); *A61B 2090/506* (2016.02)

(58) Field of Classification Search
CPC ... A61B 90/50; A61B 2090/506; A61B 19/00; F16M 13/027; F16M 11/18; F16M 11/10;
(Continued)

(56) References Cited

U.S. PATENT DOCUMENTS 6,788,018 B1 9/2004 Blumenkranz
7,562,851 B2 * 7/2009 Hein .................. F16M 11/2014
248/276.1

(Continued)

FOREIGN PATENT DOCUMENTS

CN    202497237 U   10/2012
CN    103142316 A    6/2013
(Continued)

OTHER PUBLICATIONS

International Search Report under date of mailing of Oct. 27, 2014 in connection with PCT/CN2014/082975.
(Continued)

*Primary Examiner* — Christopher E Garft
(74) *Attorney, Agent, or Firm* — Quarles & Brady LLP

(57) ABSTRACT

The present invention relates to a medical pendant lifting system, comprising a main frame, a driving device, a transmission device, a main body component, a first connecting rod, a second connecting rod, a third connecting rod and a connecting head, wherein the driving device drives the main body component and the third connecting rod via the transmission device; the driving device is connected to the main frame by a first rotating shaft; the main body component is connected to the main frame by a third rotating shaft, connected to the output component of the transmission device by a second rotating shaft, connected to the connecting head by a fifth rotating shaft, and connected to the second connecting rod by a sixth rotating shaft; the third connecting rod is connected to the main frame by a fourth
(Continued)

rotating shaft, and connected to the second connecting rod by a seventh rotating shaft; the first connecting rod is connected to the second connecting rod by a ninth rotating shaft, and connected to the connecting head by an eighth rotating shaft; and the first to ninth rotating shafts are parallel to each other, the third, the fourth, the sixth, and the seventh rotating shafts form a first parallelogram, and the fifth, the sixth, the eighth, and the ninth rotating shafts form a second parallelogram. The present invention has the beneficial technical effects of being convenient in wiring and pipe arrangement and having a large lifting height.

10 Claims, 4 Drawing Sheets

(58) Field of Classification Search
CPC .......... F16M 2200/063; F16M 2200/06; F21V 21/26
USPC ............................................... 248/284.1, 327
See application file for complete search history.

(56) References Cited

U.S. PATENT DOCUMENTS

| | | | | |
|---|---|---|---|---|
| 7,992,832 | B2* | 8/2011 | Zhang | F16M 11/10 248/281.11 |
| 2006/0291044 | A1 | 12/2006 | Nozawa | |
| 2007/0080275 | A1* | 4/2007 | Stachowski | A61B 8/00 248/323 |
| 2007/0156122 | A1* | 7/2007 | Cooper | B25J 19/0016 606/1 |
| 2012/0088963 | A1* | 4/2012 | Yasunaga | A61B 1/00149 600/102 |
| 2013/0034347 | A1* | 2/2013 | Randy | F16M 11/2085 396/428 |
| 2013/0140412 | A1* | 6/2013 | Hirose | A61B 1/00149 248/124.1 |
| 2013/0140424 | A1* | 6/2013 | Frick | F16M 11/00 248/550 |
| 2015/0308610 | A1* | 10/2015 | Zhao | A61B 8/4405 600/459 |
| 2015/0342692 | A1* | 12/2015 | Yi | A61B 90/30 248/123.11 |
| 2017/0020280 | A1* | 1/2017 | Chuang | A47B 9/16 |

FOREIGN PATENT DOCUMENTS

| | | |
|---|---|---|
| DE | 83 09 857 U1 | 9/1986 |
| DE | 197 42 051 A1 | 3/1999 |
| JP | 2005013588 A | 1/2005 |
| JP | 2005137932 A | 6/2005 |

OTHER PUBLICATIONS

Supplementary European Search Report issued in corresponding European Patent Application No. 14 83 2085, mailed Feb. 17, 2017, 6 pages.

* cited by examiner

MEDICAL PENDANT LIFTING SYSTEM

CROSS-REFERENCE TO RELATED APPLICATIONS

The present application represents the national stage entry of PCT International Patent Application No. PCT/CN2014/082975 filed on Jul. 25, 2014, which claims priority of Chinese patent application No. 201310333198 0.0 filed on Aug. 2, 2013 and Chinese patent application No. 201410339398.1 filed on Jul. 16, 2014, the disclosures of which are incorporated herein by reference in its their entirety for all purposes.

TECHNICAL FIELD

The present invention relates to the technical field of medical equipment, and more particularly to a medical pendant lifting system.

BACKGROUND ART

Medical pendant system is indispensable medical equipment used in operating rooms, intensive care units and the like in modern hospitals. A medical pendant lifting system is an important part of a medical pendant.

The existing medical pendant lifting systems mainly have the defects of being inconvenient in wiring and pipe arrangement and having an insufficient lifting height.

SUMMARY OF THE INVENTION

An objective of the present invention is to overcome the above defects of the existing medical pendant lifting systems and provide a medical pendant lifting system which is convenient in wiring and pipe arrangement and has a large lifting height.

The above objective of the present invention is achieved by means of a medical pendant lifting system. Said medical pendant lifting system comprises a main frame, a driving device, a transmission device, a main body component, a first connecting rod, a second connecting rod, a third connecting rod, and a connecting head, wherein said main frame is fixed to a base; said driving device drives said main body component and third connecting rod via said transmission device; said transmission device comprises an input component and an output component; said connecting head is fixed to a medical pendant body;

said driving device is connected to said main frame by a first rotating shaft;

said main body component is connected to said main frame by a third rotating shaft; said main body component is connected to the output component of said transmission device by a second rotating shaft; said main body component is connected to said connecting head by a fifth rotating shaft; said main body component is connected to said second connecting rod by a sixth rotating shaft;

said third connecting rod is connected to said main frame by a fourth rotating shaft; said third connecting rod is connected to said second connecting rod by a seventh rotating shaft;

said first connecting rod is connected to said second connecting rod by a ninth rotating shaft; said first connecting rod is connected to said connecting head by an eighth rotating shaft; and said first, second, third, fourth, fifth, sixth, seventh, eighth and ninth rotating shafts are parallel to each other, and when viewing from a section vertically passing through said first to ninth rotating shafts, said third, fourth, sixth, and seventh rotating shafts forming a first parallelogram, and said fifth, sixth, eighth, and ninth rotating shafts forming a second parallelogram.

According to the technical solution described above, the medical pendant lifting system of the present invention has the beneficial technical effects of being convenient in wiring and pipe arrangement and having a large lifting height.

The medical pendant lifting system of the present invention can also have the beneficial technical effects of modularizing the components thereof, improving the threading capacity, reducing the power consumption, decreasing the projected area, simplifying the structure of the product, and improving the load capacity.

Preferably, said driving device is an electric motor.

According to the technical solution described above, the medical pendant lifting system of the present invention has the beneficial technical effects of effectively reducing the power consumption, simplifying the structure of the product and improving the load capacity by choosing a suitable driving device.

Preferably, said transmission device is a screw-nut transmission device, i.e., the input component of said transmission device is a screw, and the output component of said transmission device is a nut.

According to the technical solution described above, the medical pendant lifting system of the present invention has the beneficial technical effect of conveniently and effectively moving the main body component and the third connecting rod up and down by choosing a suitable transmission device.

Preferably, said medical pendant lifting system further comprises a decelerating device arranged between said driving device and said transmission device.

According to the technical solution described above, the medical pendant lifting system of the present invention has the beneficial technical effect of reducing the output of the driving device so as to stabilize the up-and-down motion of the connecting head.

Preferably, said main body component comprises a front engaging block, a hollow beam, a first rear engaging block and a second rear engaging block, wherein said front engaging block is arranged at the front side of said hollow beam and connected to said main frame by the third rotating shaft and connected to the output component of said transmission device by the second rotating shaft; said first rear engaging block is arranged at the upper rear side of said hollow beam and connected to said second connecting rod by the sixth rotating shaft; and said second rear engaging block is arranged at the lower rear side of said hollow beam and connected to said connecting head by the fifth rotating shaft.

According to the technical solution described above, the medical pendant lifting system of the present invention has the beneficial technical effects of effectively facilitating the wiring and pipe arrangement and improving the lifting height by choosing a suitable design of the main body component.

Preferably, said medical pendant lifting system further comprises a level adjusting device for adjusting a lower surface of said connecting head to a level position, and said level adjusting device is arranged between said main body component and said sixth rotating shaft.

According to the technical solution described above, the medical pendant lifting system of the present invention has the beneficial technical effect of simply and rapidly adjusting the level of the lower surface of the connecting head.

Preferably, said first connecting rod, second connecting rod and third connecting rod all comprise paired connecting rods.

According to the technical solution described above, the medical pendant lifting system of the present invention has the beneficial technical effect of making the whole connecting rod structure and the whole medical pendant lifting system more stable.

Preferably, said medical pendant lifting system further comprises an electric motor supporting block, to which said electric motor is fixed and which is connected to said main frame by the first rotating shaft.

According to the technical solution described above, the medical pendant lifting system of the present invention has the beneficial technical effect of mounting the electric motor more stably.

Preferably, said medical pendant lifting system further comprises a travel switch bracket fixed to said electric motor supporting block and provided with an upper travel switch and a lower travel switch.

According to the technical solution described above, the medical pendant lifting system of the present invention has the beneficial technical effect of limiting the up-and-down travel of the nut so as to control the moving distance of the medical pendant lifting system, i.e., the lifting height of the connecting head.

Preferably, said screw is a ball screw.

According to the technical solution described above, the medical pendant lifting system of the present invention has the beneficial technical effect of effectively reducing the frictional resistance between the screw and the nut.

LIST FOR REFERENCE NUMERALS

1. Main frame;
2. Driving device;
3. Transmission device;
4. Main body component;
5. Connecting head;
6. Decelerating device;
7. Level adjusting device;
11. First connecting rod;
12. Second connecting rod;
13. Third connecting rod;
21. Electric motor;
22. Electric motor supporting block;
23. Travel switch bracket;
24. Upper travel switch;
25. Lower travel switch;
31. Screw;
32. Nut;
41. Front engaging block;
42. Hollow beam;
43. First rear engaging block;
44. Second rear engaging block;
100. Medical pendant lifting system;
S1. First rotating shaft;
S2. Second rotating shaft;
S3. Third rotating shaft;
S4. Fourth rotating shaft;
S5. Fifth rotating shaft;
S6. Sixth rotating shaft;
S7. Seventh rotating shaft;
S8. Eighth rotating shaft;
S9. Ninth rotating shaft.

DETAILED DESCRIPTION

The present invention is further described in connection with drawings and particular embodiments as follows and is elaborated in more detail in the following description in order to be fully understood, but it is apparent that the present invention can be implemented in many other ways different from those described herein; generalization and deduction can be made by a person skilled in the art without departing from the connotation of the invention according to practical application, and therefore the scope of protection of the present invention should not be limited by the specific content of embodiments of the present invention herein.

Figure 1:
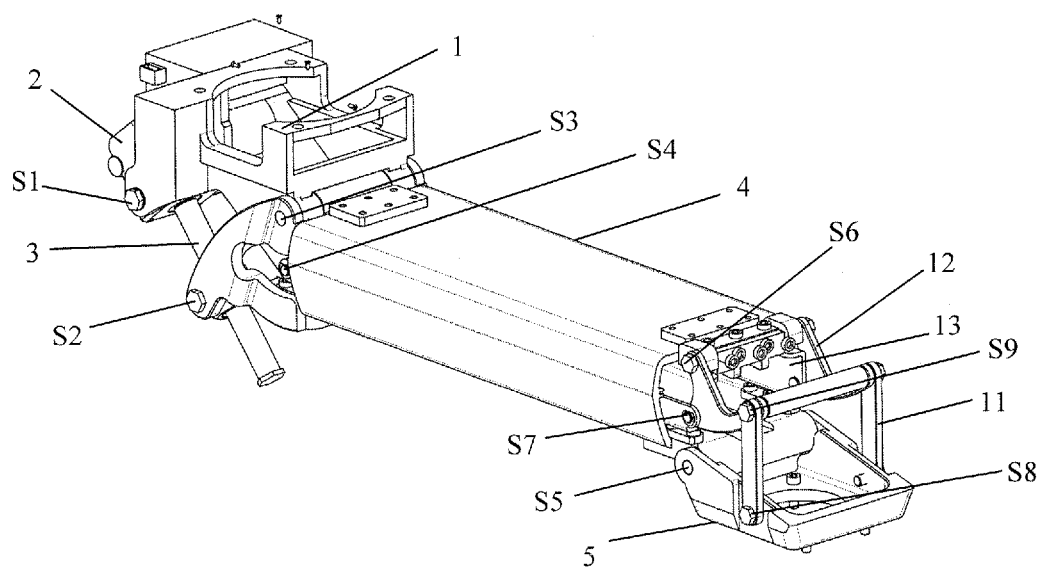
FIG. 1 shows a perspective schematic diagram in a first view of a medical pendant lifting system of the present invention.
Figure 2:
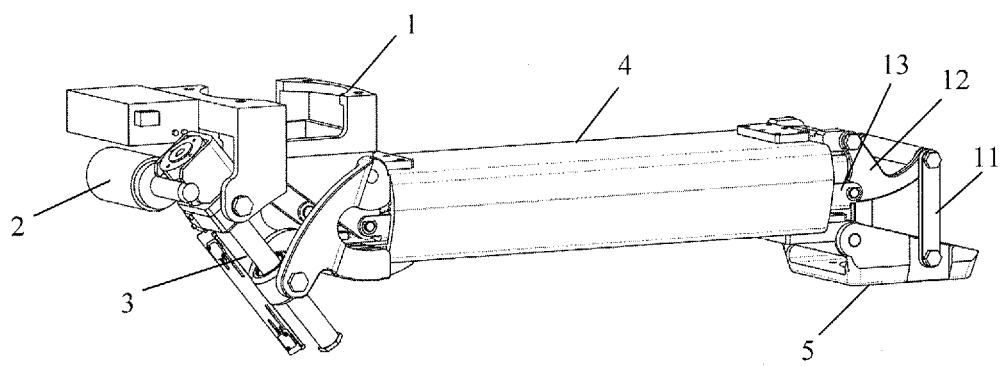
FIG. 2 shows a perspective schematic diagram in a second view of a medical pendant lifting system of the present invention.
Figure 3:
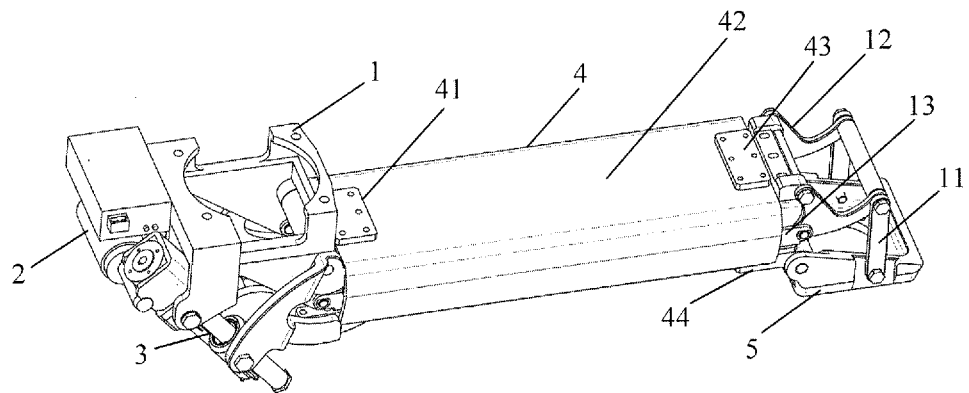
FIG. 3 shows a perspective schematic diagram in a third view of a medical pendant lifting system of the present invention.
Figure 4:
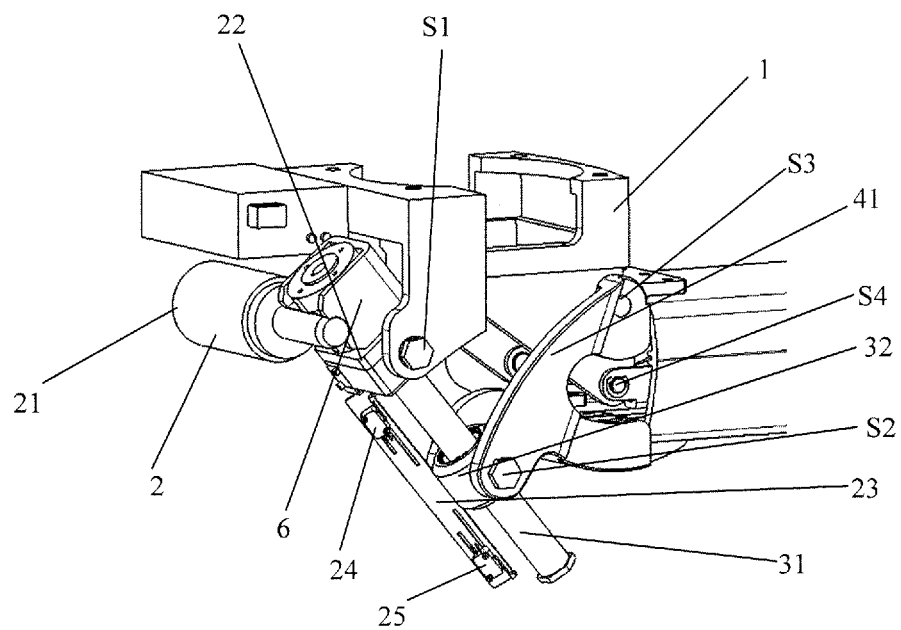
FIG. 4 shows a schematic diagram of a front side partial structure of a medical pendant lifting system of the present invention.
Figure 5:
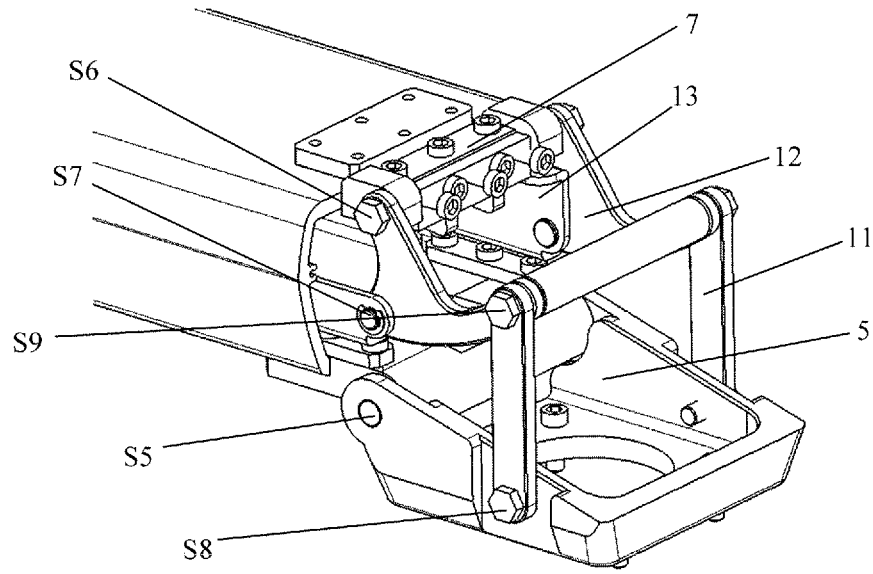
FIG. 5 shows a schematic diagram of a rear side partial structure of a medical pendant lifting system of the present invention.
Figure 6:
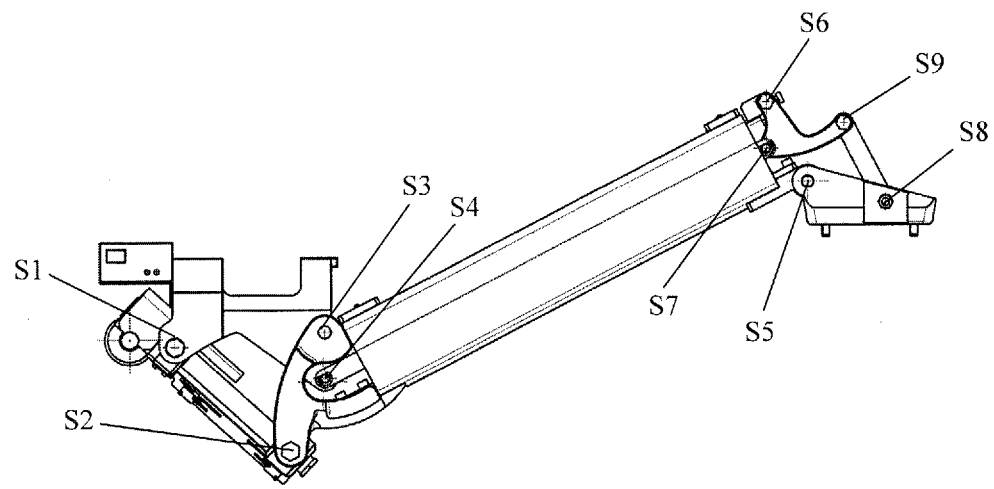
FIG. 6 shows a schematic diagram of a medical pendant lifting system of the present invention, when the connecting head is located at the highest point.
Figure 7:
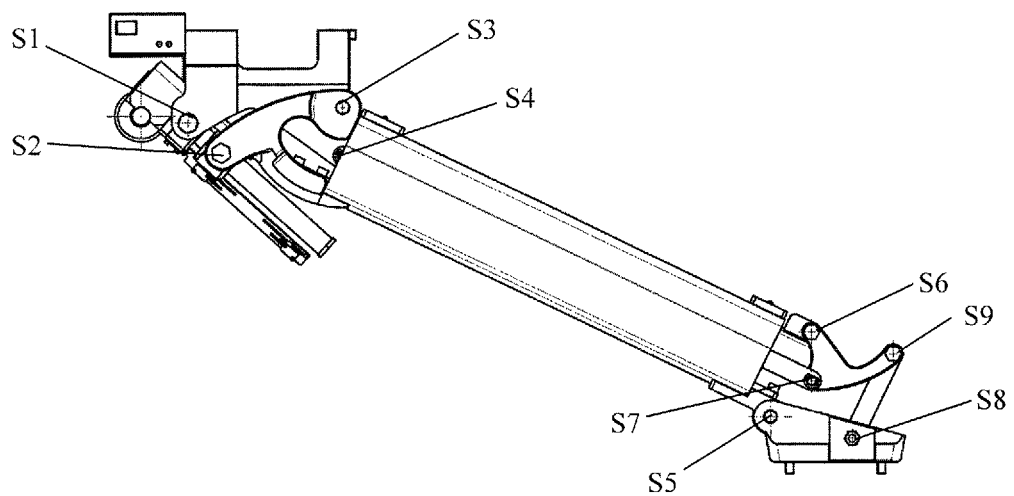
FIG. 7 shows a schematic diagram of a medical pendant lifting system of the present invention, when the connecting head is located at the lowest point.

FIG. 1 shows a perspective schematic diagram in a first view of a medical pendant lifting system of the present invention. FIG. 2 shows a perspective schematic diagram in a second view of a medical pendant lifting system of the present invention. FIG. 3 shows a perspective schematic diagram in a third view of a medical pendant lifting system of the present invention. FIG. 4 shows a schematic diagram of a front side partial structure of a medical pendant lifting system of the present invention. FIG. 5 shows a schematic diagram of a rear side partial structure of a medical pendant lifting system of the present invention. FIG. 6 shows a schematic diagram of a medical pendant lifting system of the present invention, when the connecting head is located at the highest point. FIG. 7 shows a schematic diagram of a medical pendant lifting system of the present invention, when the connecting head is located at the lowest point.

A medical pendant lifting system 100 of the present invention comprises a main frame 1, a driving device 2, a transmission device 3, a main body component 4, a first connecting rod 11, a second connecting rod 12, a third connecting rod 13 and a connecting head 5, wherein the main frame 1 is fixed to a base (not shown); the driving device 2 drives the main body component 4 and the third connecting rod 13 via the transmission device 3; the transmission device 3 comprises an input component and an output component; and the connecting head 5 is fixed to the medical pendant body (not shown).

The base can be any seat part for fixing the main frame. Preferably, the base can be, for example, a top structure in the mounting space of the medical pendant lifting system, such as the ceiling of an operating room or an intensive care unit in a hospital. Preferably, the base also can be, for example, a lower end of an upper arm mounted on the top structure of the room, e.g., on the ceiling. Preferably, the main frame 1 is fixed to the base by means of, for example, anchor plates and screws.

The driving device 2 is connected to the main frame 1 by a first rotating shaft S1. Therefore, the driving device 2 can rotate about the first rotating shaft S1.

The main body component 4 is connected to the main frame 1 by a third rotating shaft S3, the main body component 4 is connected to the output component of the transmission device 3 by a second rotating shaft S2, the main body component 4 is connected to the connecting head 5 by a fifth rotating shaft S5, and the main body component 4 is connected to the second connecting rod 12 by a sixth rotating shaft S6.

Therefore, the main body component 4 can rotate about the third rotating shaft S3, the output component of the transmission device 3 can rotate about the second rotating shaft S2, the connecting head 5 can rotate about the fifth rotating shaft S5, and the second connecting rod 12 can rotate about the sixth rotating shaft S6.

The third connecting rod 13 is connected to the main frame 1 by a fourth rotating shaft S4, and the third connecting rod 13 is connected to the second connecting rod 12 by a seventh rotating shaft S7.

Therefore, the third connecting rod 13 can rotate about the fourth rotating shaft S4, and the second connecting rod 12 and the third connecting rod 13 can rotate about the seventh rotating shaft S7.

The first connecting rod 11 is connected to the second connecting rod 12 by the ninth rotating shaft S9, and the first connecting rod 11 is connected to the connecting head 5 by the eighth rotating shaft S8.

Therefore, first connecting rod 11 and the second connecting rod 12 can rotate about the ninth rotating shaft S9, and the first connecting rod 11 and the connecting head 5 can rotate about the eighth rotating shaft S8.

The first rotating shaft S1, the second rotating shaft S2, the third rotating shaft S3, the fourth rotating shaft S4, the fifth rotating shaft S5, the sixth rotating shaft S6, the seventh rotating shaft S7, the eighth rotating shaft S8, and the ninth rotating shaft S9 are parallel to each other, and when viewing from a section vertically passing through the first to ninth rotating shafts S1-S9, the third rotating shaft S3, the fourth rotating shaft S4, the sixth rotating shaft S6, and the seventh rotating shaft S7 form a first parallelogram, and the fifth rotating shaft S5, the sixth rotating shaft S6, the eighth rotating shaft S8, and the ninth rotating shaft S9 form a second parallelogram.

That is to say, when viewing from the section vertically passing through the first to ninth rotating shafts S1-S9 (e.g., see FIGS. 6 and 7), the first to ninth rotating shafts S1-S9 are in the form of dots or round dots in the cross-sectional view, the third rotating shaft S3, the fourth rotating shaft S4, the sixth rotating shaft S6, and the seventh rotating shaft S7 form the four vertexes of the first parallelogram, and the fifth rotating shaft S5, the sixth rotating shaft S6, the eighth rotating shaft S8, and the ninth rotating shaft S9 form the four vertexes of the second parallelogram.

Therefore, the whole medical pendant lifting system forms a double-parallelogram structure. The driving device 2 drives a driving component 4 via the transmission device 3, i.e., drives one side of the first parallelogram (the side formed by the third rotating shaft S3 and the sixth rotating shaft S6), so as to finally drive one side of the second parallelogram (the side formed by the fifth rotating shaft S5 and the eighth rotating shaft S8) and keep the side to be at the same angle as the level line, i.e., to keep the lower surface of the connecting head 5 at the level.

Thus, the medical pendant lifting system of the present invention has the beneficial technical effects of being convenient in wiring and pipe arrangement, having a large lifting height, modularizing the components thereof, improving the threading capacity, reducing the power consumption, decreasing the projected area, simplifying the structure of the product, and improving the load capacity.

It should be noted that the expressions such as "upper", "lower", "front", "rear", "left", and "right" used herein are exemplary directions defined only for facilitating the description of the present invention. For example, as shown in FIGS. 6 and 7, the upper side direction of the paper plane is "upper", the lower side direction of the paper plane is "lower", the left side direction of the paper plane is "front", and the right side direction of the paper plane is "rear". Of course, on the basis of the present invention, a person skilled in the art would be able to understand that the directions such as "upper", "lower", "front", "rear", "left", and "right" can be defined in other ways, which also fall within the scope of protection of the present invention.

Preferably, the driving device 2 is an electric motor 21.

Certainly, a person skilled in the art should understand that other driving devices, e.g., a hydraulic driving device, can also be used, so long as it can drive the medical pendant lifting system. Such variations also fall into the protection scope of the present invention.

Preferably, the transmission device 3 is a screw-nut transmission device. That is to say, the input component of the transmission device 3 is a screw 31, and the output component of the transmission device 3 is a nut 32. Preferably, the screw 31 is a ball screw.

In the preferable embodiment, the outer side of the nut 32 is fixed to a front engaging block 41 by the second rotating shaft S2, and the nut 32 can rotate about the second rotating shaft S2. The inner side of the nut 32 cooperates with the screw 31, and when a power source drives the electric motor 21 and the decelerating device 6 to drive the nut 32 via the screw 31, the nut 32 moves up and down along the screw 31 and thus drives the main body component 4 to rotate about the third rotating shaft S3, so as to achieve the purpose of raising and lowering the same.

Certainly, a person skilled in the art should understand that the other transmission device, e.g., a gear plate-gear transmission device, can also be used, so long as it can transform the motion from one form (e.g., rotation) to another form (e.g., translation). Such variations also fall into the protection scope of the present invention.

Preferably, the medical pendant lifting system 100 further comprises a decelerating device 6, and the decelerating device 6 is arranged between the driving device 2 and the transmission device 3. Preferably, the decelerating device 6 is, for example, a reduction box.

Preferably, the main body component 4 can comprise a front engaging block 41, a hollow beam 42, a first rear engaging block 43 and a second rear engaging block 44, wherein the front engaging block 41 is arranged at the front side of the hollow beam 42 and connected to the main frame 1 by the third rotating shaft S3 and to the output component of the transmission device 3 by the second rotating shaft S2; the first rear engaging block 43 is arranged at the upper rear side of the hollow beam 42 and connected to the second connecting rod 12 by the sixth rotating shaft S6; and the second rear engaging block 44 is arranged at the lower rear side of the hollow beam 42 and connected to the connecting head 5 by the fifth rotating shaft S5.

Preferably, the medical pendant lifting system 100 further comprises a level adjusting device 7 for adjusting the lower surface of the connecting head 5 to a level position, and the level adjusting device 7 is arranged between the main body component 4 and the sixth rotating shaft S6.

Preferably, the level adjusting device 7 is arranged so that the adjusting member is pushed by three set screws, fastened by two screws after it is in position, and finally reinforced and fixed at the upper end surface thereof by three screws.

Certainly, on the basis of the present invention, a person skilled in the art should understand that the number of the screws used in the level adjusting device of the present invention is not limited to two or three, and other numbers such as one, four . . . can also be used. Various numbers of the screws fall within the scope of protection of the present invention, so long as they can achieve the effective adjustment of the level position of the lower surface of the connecting head.

Preferably, the first connecting rod 11, the second connecting rod 12, and the third connecting rod 13 all comprise paired connecting rods. That is to say, the first connecting rod 11 can comprise paired first connecting rods, e.g., as shown in FIG. 5, respectively arranged at the left and right sides in the figure; the second connecting rod 12 can comprise paired second connecting rods, e.g., as shown in FIG. 5, respectively arranged at the left and right sides in the figure; and the third connecting rod 13 can comprise paired third connecting rods, e.g., as shown in FIG. 5, respectively arranged at the left and right sides in the figure.

Preferably, the medical pendant lifting system 100 further comprises an electric motor supporting block 22, the electric motor 21 is fixed to the electric motor supporting block 22, and the electric motor supporting block 22 is connected to the main frame 1 by the first rotating shaft S1.

Preferably, the medical pendant lifting system 100 further comprises a travel switch bracket 23 fixed to the electric motor supporting block 22, and the travel switch bracket is provided with an upper travel switch 24 and a lower travel switch 25.

That is to say, the moving range of the nut 32 is defined by the upper travel switch 24 and the lower travel switch 25 and is located between the upper travel switch 24 and the lower travel switch 25.

As shown in FIGS. 6 and 7, the medical pendant lifting system 100 of the present invention operates in such a way that the power source drives the electric motor 21 and the decelerating device 6 to drive the nut 32 via the screw 31, so that the hollow beam 42 swings up and down about the third rotating shaft S3 on the main frame 1. At the same time, the third connecting rod 13 moves up and down along with the hollow beam 42 in parallel and about the first rotating shaft S1 on the main frame 1, so as to drive the second connecting rod 12 to drive the motion of the first connecting rod 11 to finally ensure that the connecting head 5, under the combined action of the fifth rotating shaft S5 and the eighth rotating shaft S8, moves up and down along with the hollow beam 42 while keeping the lower surface at the level position.

When the nut 32 is driven by the electric motor 21 and reaches the upper travel switch 24, the connecting head 5 is located at the lowest point, as shown in FIG. 7. When the nut 32 is driven by the electric motor 21 and reaches the lower travel switch 25, the connecting head is located at the highest point, as shown in FIG. 6.

The present invention has been described by way of example above in connection with the figures, although the specific implementations of the present invention are not limited to the above embodiments. Various modifications or variations can be made by a person skilled in the art without departing from the technical concept of the present invention, and such modifications or variations of course fall within the protection scope of the present invention.

The invention claimed is:

1. A medical pendant lifting system, characterized in that said medical pendant lifting system comprises a main frame, a driving device, a transmission device, a main body component, a first connecting rod, a second connecting rod, a third connecting rod, and a connecting head, wherein said main frame is fixed to a base; said driving device drives said main body component and third connecting rod via said transmission device; said transmission device comprises an input component and an output component; said connecting head is fixed to a medical pendant body;

said driving device is connected to said main frame by a first rotating shaft;

said main body component is connected to said main frame by a third rotating shaft; said main body component is connected to the output component of said transmission device by a second rotating shaft; said main body component is connected to said connecting head by a fifth rotating shaft; said main body component is connected to said second connecting rod by a sixth rotating shaft;

said third connecting rod is connected to said main frame by a fourth rotating shaft; said third connecting rod is connected to said second connecting rod by a seventh rotating shaft;

said first connecting rod is connected to said second connecting rod by a ninth rotating shaft; said first connecting rod is connected to said connecting head by an eighth rotating shaft;

said first, second, third, fourth, fifth, sixth, seventh, eighth and ninth rotating shafts are parallel to each other, and when viewing from a section vertically passing through said first to ninth rotating shafts, said third, fourth, sixth, and seventh rotating shafts form a first parallelogram, and said fifth, sixth, eighth, and ninth rotating shafts form a second parallelogram.

2. The medical pendant lifting system of claim 1, wherein said driving device is an electric motor.

3. Wherein said transmission device is a screw-nut transmission device, i.e., the input component of said transmission device is a screw, and the output component of said transmission device is a nut.

4. The medical pendant lifting system of claim 1, wherein said medical pendant lifting system further comprises a decelerating device arranged between said driving device and said transmission device.

5. The medical pendant lifting system of claim 1, wherein said main body component comprises a front engaging block, a hollow beam, a first rear engaging block and a second rear engaging block, wherein said front engaging block is arranged at the front side of said hollow beam and connected to said main frame by the third rotating shaft and connected to the output component of said transmission device by the second rotating shaft; said first rear engaging block is arranged at the upper rear side of said hollow beam and connected to said second connecting rod by the sixth rotating shaft; and said second rear engaging block is arranged at the lower rear side of said hollow beam and connected to said connecting head by the fifth rotating shaft.

6. The medical pendant lifting system of claim 1, wherein said medical pendant lifting system further comprises a level adjusting device for adjusting a lower surface of said connecting head to a level position, and said level adjusting device is arranged between said main body component and said sixth rotating shaft.

7. The medical pendant lifting system of claim 1, wherein said first connecting rod, second connecting rod and third connecting rod all comprise paired connecting rods.

8. The medical pendant lifting system of claim 3, wherein said medical pendant lifting system further comprises an electric motor supporting block, to which said electric motor is fixed and which is connected to said main frame by the first rotating shaft.

9. The medical pendant lifting system of claim 8, wherein said medical pendant lifting system further comprises a travel switch bracket fixed to said electric motor supporting block and provided with an upper travel switch and a lower travel switch.

10. The medical pendant lifting system of claim 3, wherein said screw is a ball screw.

\* \* \* \* \*